US008697637B2

(12) United States Patent
Misse Brumas et al.

(10) Patent No.: US 8,697,637 B2
(45) Date of Patent: Apr. 15, 2014

(54) ANTIMICROBIAL PEPTIDES OF THE CECROPIN FAMILY AND THERAPEUTIC USES THEREOF

(75) Inventors: Marthe Dorothée Misse Brumas, Teyran (FR); Natthanej Luplertlop, Ka-Sor Nonthaburi (TH); Hans Yssel, Sussargues (FR); Frédéric Thomas, Montpellier (FR); François Renaud, Montpellier (FR)

(73) Assignee: Institut de Recherche pour le Developpement (IRD) (FR)

( * ) Notice: Subject to any disclaimer, the term of this patent is extended or adjusted under 35 U.S.C. 154(b) by 0 days.

(21) Appl. No.: 13/576,177

(22) PCT Filed: Feb. 3, 2011

(86) PCT No.: PCT/IB2011/050465
§ 371 (c)(1),
(2), (4) Date: Aug. 23, 2012

(87) PCT Pub. No.: WO2011/095939
PCT Pub. Date: Aug. 11, 2011

(65) Prior Publication Data
US 2012/0316102 A1   Dec. 13, 2012

(30) Foreign Application Priority Data

Feb. 3, 2010 (FR) .................................. 10 00434

(51) Int. Cl.
*A61P 31/12*   (2006.01)
*C07K 14/435*   (2006.01)

(52) U.S. Cl.
CPC ................................. *C07K 14/435* (2013.01)
USPC ........................................................ 514/2.4

(58) Field of Classification Search
None
See application file for complete search history.

(56) References Cited

U.S. PATENT DOCUMENTS

2011/0039761 A1*   2/2011   Eckert et al. .................. 514/2.4

FOREIGN PATENT DOCUMENTS

WO   WO-03/008442 A1   1/2003

OTHER PUBLICATIONS

Lowenberger et al. ("Antimicrobial Activity Spectrum, cDNA Cloning, and mRNA Expression of Newly Isolated Member of the Cecropin Family from the Mosquito Vector *Aedes aegypti*" (Jul. 16, 1999) Journal of Biological Chemistry 274(29):20092-20097).*
Nene et al ("Genome Sequence of *Aedes aegypti*, a Major Arbovirus Vector" (Jun. 22, 2007) Science 316: 1718-1723).*
Database UniProt [Online] Jul. 25, 2006, Nene V. et al.: "Genome sequence of *Aedes aegypti*", XP002598498, EBI Database accession No. Q17NR1.
Lowenberger C et al: "Antimicrobial Activity Spectrum, cDNA Cloning, and mRNA Expression of a Newly Isolated Member of the Cecropin Family from Mosquito Vector *Aedes aegypti*", Journal of Biological Chemistry, American Society for Biochemistry and Molecular Biology, Inc, vol. 274, No. 29, Jul. 16, 1999, pp. 20092-20097, XP002165176.
Sun D. et al.: "Peptide sequence of an antibiotic cecropin from the vector mosquito, *Aedes albopictus*", Biochem. Biophys. Res. Comm., vol. 249, 1998, pp. 410-415, XP002598499.
Translation of the Written Opinion of the International Searching Authority dated Sep. 27, 2012.
International Preliminary Report and Written Opinion, dated Sep. 18, 2012.

* cited by examiner

*Primary Examiner* — Jean Witz
*Assistant Examiner* — Mindy Newman
(74) *Attorney, Agent, or Firm* — Novak Druce Connolly Bove + Quigg LLP

(57) ABSTRACT

The present invention relates to an antimicrobial peptide characterised in that said peptide includes the sequence SEQ ID No. 1 or the sequence SEQ ID No. 2, the sequence SEQ ID No. 2 representing a fragment of the sequence SEQ ID No. 1, for use as a drug. Advantageously according to the invention, the peptide having sequence SEQ ID No. 1 is used specifically for treating bacterial, viral and/or parasitic infections, and the peptide having sequence SEQ No. 2 is used for treating bacterial and/or viral infections.

19 Claims, 4 Drawing Sheets

Figure 5

Inhibition of the infection of HEK-293T cells by the chikungunya 147-2 virus

ANTIMICROBIAL PEPTIDES OF THE CECROPIN FAMILY AND THERAPEUTIC USES THEREOF

RELATED APPLICATIONS

This application is a national stage application under 35 U.S.C. §371 of PCT/IB2011/050465, filed Feb. 3, 2011, which claims priority of French application 10/00434, filed Feb. 3, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Replacement_Sequence Listing_21029-00403-U.S. ST25.txt. The size of the text file is 1.79 KB; the text file was created on Jul. 27, 2012.

The present invention relates to antimicrobial peptides for use as a medicament for antibacterial, antiviral and/or antiparasitic control purposes.

Antimicrobial peptides denote a vast group of peptides (more than 500 peptides have been identified to date) having on average from 20 to 50 amino acids, which share a cationic nature and amphiphilic properties. Their structural diversity is great, at the origin of three large families of cationic antimicrobial peptides. The cecropins were the first cationic microbial peptides to be wholly characterised, starting from nymphs of the *Hyalophora cecropia* moth, at the start of the 1980s by H. Boman (J. Intern. Med. 2003; 254: 197-215).

The cationic antimicrobial peptides are considered to be one of the key elements of the innate immune system, which provides the first line of defence of multicellular organisms.

The use of insect antimicrobial peptides, which are natural substances produced by insects, and the use of their derivatives are currently in the course of clinical development, substantially in topical form (reduction of local microbial flora in order to prevent the occurrence of infections: "Andrès and Dimarcq, *Med Mal Infect* 2007; 37: 194-199").

In both human and animal health, in the face of the emergence of new pathogens and especially of multiresistant microorganisms, the need to find molecules with which bacterial, viral and parasitic infections can be controlled is growing, and pharmaceutical manufacturers are becoming increasingly more interested in molecules which have a broad spectrum of activity.

Accordingly, it is an object of the present invention in particular to provide molecules which have a broad spectrum of activity.

More particularly, it is an object of the invention to provide molecules which allow bacterial, viral and also parasitic infections, or at least two of said infections, to be controlled.

It has surprisingly been found by the inventors that the object of the present invention can be achieved by natural antimicrobial peptides of insects, namely antimicrobial peptides of *Aedes aegypti*.

Among the antimicrobial peptides of *Aedes aegypti* provided by the present invention, the peptide of sequence SEQ ID No.1 as defined below has already been described in the literature as belonging to the family of the cecropins and as being a putative antibacterial peptide However, no function has as yet been demonstrated regarding that peptide.

With regard to the peptides of the cecropin family, some of them have been described in the literature as having an activity for the treatment of leishmaniasis. Thus, documents "WO03008442", "Biochem J. 1998 Feb. 15, 330 (Pt 1): 453-60", "Biochem J. 2003 Oct. 1, 375 (Pt 1): 221-30", "Protein Pept Lett. 2004 April 11(2): 115-24", "Antimicrob Agents Chemother. 2004 February 48 (2): 641-3" and "Antimicrob Agents Chemother. 2001 September 45(9): 2441-9" all describe the use of cecropin-melittin hybrid peptides for the treatment of leishmaniasis.

The peptide of sequence SEQ ID No. 1 is the immature peptide which comprises the signal peptide. Cleavage of the signal peptide allows the secreted peptide or mature peptide to be obtained.

The inventors have been able to establish that the signal peptide corresponds to the peptide of sequence SEQ ID No. 3 as defined below, and they have thus been able to establish that the mature or secreted peptide corresponds to the peptide of sequence SEQ ID No. 2 as defined below.

In the prior art, tests of the efficacy of peptides are conventionally carried out on the secreted peptides, that is to say on the peptides without their signal peptide. Accordingly, the activity tests carried out in the present patent application were carried out on the peptide of sequence SEQ ID No. 2.

However, an original feature of the inventors' work was to test the efficacy of a natural insect antimicrobial peptide also with its signal peptide, which had never been done before.

Accordingly, it has surprisingly been found by the inventors that the peptide of sequence SEQ ID No. 1 is particularly interesting as far as its activity is concerned, because it exhibits antibacterial, antiparasitic and also antiviral activities.

It has accordingly been possible to establish that the immature peptide (of sequence SEQ ID No. 1) does not behave in the same manner as the mature peptide (of sequence SEQ ID No. 2). The peptide of sequence SEQ ID No. 1 in fact exhibits a more pronounced viral activity than that of the peptide of sequence SEQ ID No. 2, while the peptide of sequence SEQ ID No. 2 exhibits a more pronounced antibacterial activity than that of the peptide of sequence SEQ ID No. 1. In addition, the peptide of sequence SEQ ID No. 2 exhibits antibacterial and antiviral activities but does not exhibit antiparasitic activity, in contrast to the peptide SEQ ID No. 1, which exhibits antibacterial, antiviral and also antiparasitic activities.

The signal peptide of sequence SEQ ID No. 3 therefore proves to be of interest as regards its functionality since it constitutes the only difference between the peptide of sequence SEQ ID No. 2 and that of sequence SEQ ID No. 1.

Accordingly, the present invention relates both to antimicrobial peptides of *Aedes aegypti* with or without the signal peptide, and to the signal peptide itself.

The sequence SEQ ID No. 1 is as follows:

MNMNFTKLFAIVLLAALVLLGQTEAGGLKKLGKKLEGAGKRVFKASEKAL
PVVVGIKAIGK

The sequence SEQ ID No. 2 is:

GGLKKLGKKLEGAGKRVFKASEKALPVVVGIKAIGK

The sequence SEQ ID No. 3 is:

MNMNFTKLFAIVLLAALVLLGQTEA

The present invention relates more particularly to an antimicrobial peptide, characterised in that it has the sequence SEQ ID No. 1 or the sequence SEQ ID No. 2, the sequence SEQ ID No. 2 representing a fragment of the sequence SEQ ID No. 1, for use as a medicament.

According to the invention, said medicament comprises a therapeutically effective amount of at least one peptide as defined above, in association with a pharmaceutically acceptable carrier.

Advantageously according to the invention, the medicament is prepared for administration by the injectable route or for administration in topical form.

More particularly, the peptide as defined above, of sequence SEQ ID No. 1 or SEQ ID No. 2, is used for the treatment of bacterial and/or viral infections.

According to an advantageous embodiment of the invention, the peptide as defined above, of sequence SEQ ID No. 1 or SEQ ID No. 2, is used more particularly for the treatment of bacterial infections and especially those caused by Gram positive and/or Gram negative bacteria.

According to another advantageous embodiment of the invention, the peptide as defined above, of sequence SEQ ID No. 1 or SEQ ID No. 2, is used more particularly for the treatment of viral infections and especially those caused by the dengue virus and/or the chikungunya virus.

Advantageously according to the invention, the peptide as defined above, of sequence SEQ ID No. 1 or SEQ ID No. 2, is used for the treatment of bacterial and viral infections.

According to another advantageous embodiment, the invention relates more particularly to the antimicrobial peptide of sequence SEQ ID No. 1, for the treatment of parasitic infections and especially those caused by the parasite *Leishmania braziliensis* and/or by the parasite *Leishmania infantum*.

Advantageously according to the invention, the peptide of sequence SEQ ID No. 1 is used for the treatment of bacterial, viral and parasitic infections.

The present invention relates further to a pharmaceutical composition, characterised in that it comprises a therapeutically effective amount of an antimicrobial peptide having the sequence SEQ ID No. 1 or SEQ ID No. 2 as defined above, in association with a pharmaceutically acceptable carrier.

Advantageously according to the invention, the pharmaceutical composition is intended for administration by the injectable route or in topical form.

Other features and advantages of the invention are given in the following description with reference to FIGS. 1 to 7.

Figure 1:
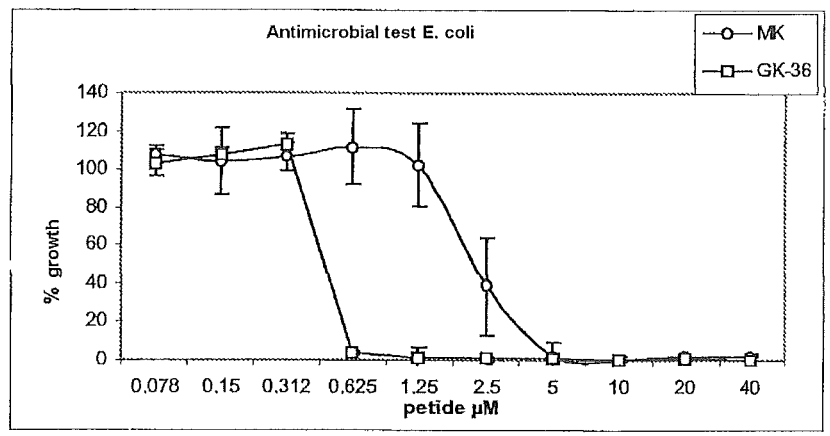
FIG. 1 shows the antimicrobial test with the Gram negative bacterium *E. coli* and the peptides "MK61" (peptide of sequence SEQ ID No. 1) and "GK36" (peptide of sequence SEQ ID No. 2).
Figure 2:
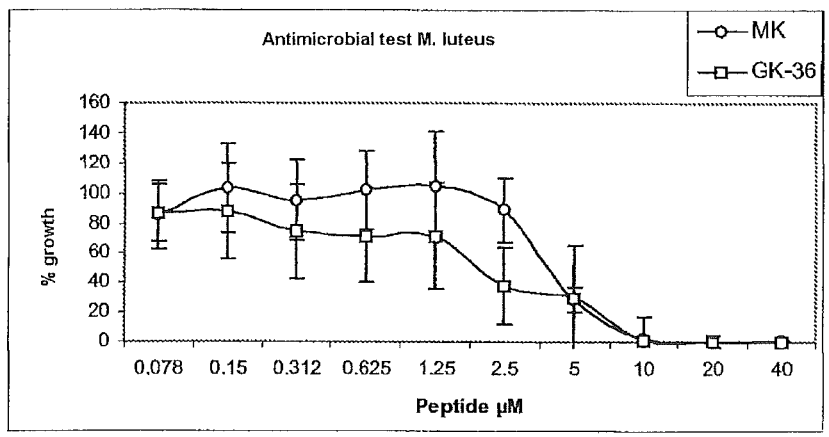
FIG. 2 shows the antimicrobial test with the Gram positive bacterium *Micrococcus luteus* and the peptides MK61 and GK36.

The y-axis of each of FIGS. 1 and 2 represents the percentage bacterial growth, and the x-axis represents the peptide concentration (µM). The symbol -o- represents the peptide MK61 and the symbol -□- represents the peptide GK36.

Figure 3:
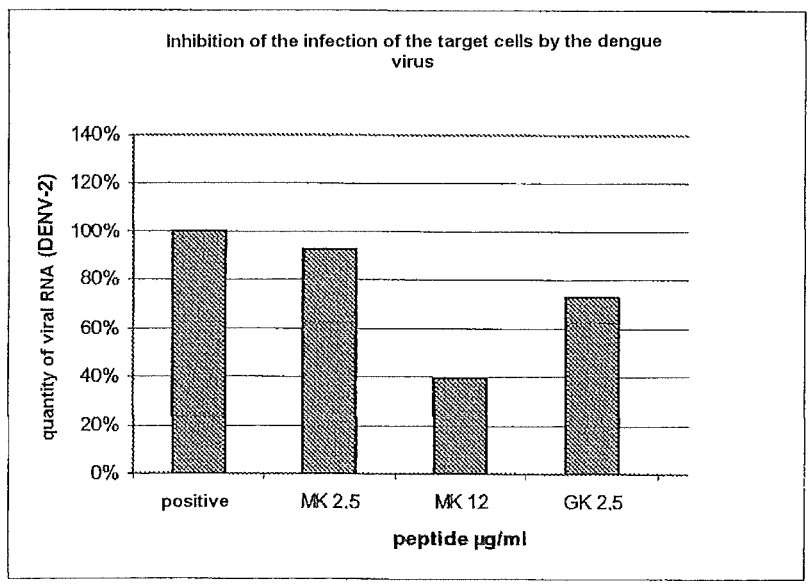

FIG. 3 is a histogram which shows the inhibition of the infection of dendritic cells by the dengue virus serotype 2 "DENV-2" with the aid of the peptides MK61 and GK36.

The y-axis represents the percentage infection of the dendritic cells by the "DENV-2" virus, and the x-axis represents the peptide concentration (µM).

The column on the far left represents the positive control when 100% of the cells are infected by DENV-2. The next two columns represent the results obtained for the peptide MK61 at a concentration of 2.5 µg/ml and at a concentration of 12 µg/ml, respectively. The column on the far right represents the result obtained for the peptide GK36 at a concentration of 2.5 µg/ml.

FIGS. 4A, 4B, 4C and 4D show the inhibition of the infection of C6/36 cells of *Aedes albopictus* mosquitoes by the dengue virus (the viruses of serotypes 1, 2, 3 and 4, respectively: "DENV-1", "DENV-2", "DENV-3" and "DENV-4") with the aid of the peptides MK61 and GK36. The peptides MK61 and GK36 are each prepared at concentrations of 5 µg/ml and 10 µg/ml and are tested after the cells have been incubated with the virus for 12 hours and 24 hours.

FIG. 5 is a histogram which shows the inhibition of the infection of HEK-293T cells by the chikungunya 147-2 virus with the aid of the peptides MK61 and GK36.

The y-axis represents the percentage infection of the HEK-293T cells by the chikungunya 147-2 virus, and the x-axis represents the peptide concentration (µM).

The peptides GK36 and MK61 are each prepared at concentrations of 10 µg/ml, 50 µg/ml and 80 µg/ml.

Figure 6:
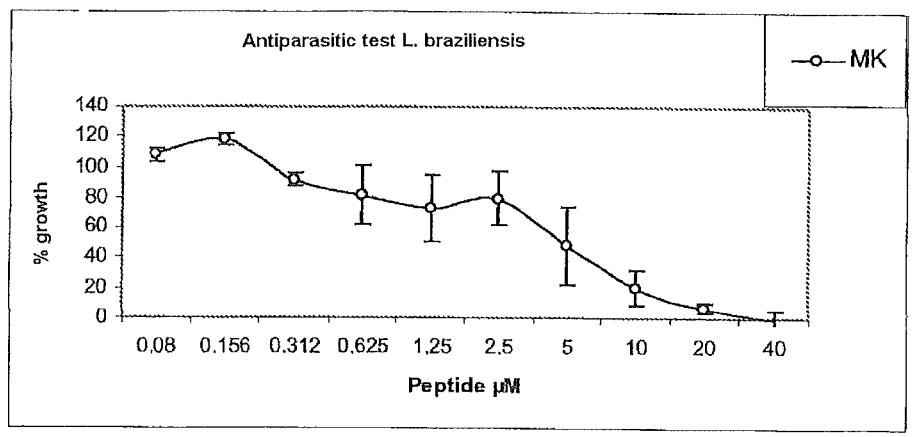
Figure 7:
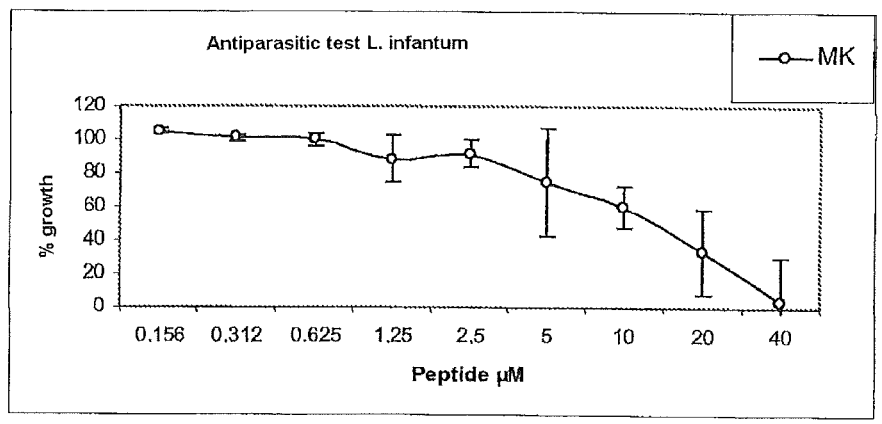

FIGS. 6 and 7 show the antiparasitic test with the peptide MK61 and the parasite *Leishmania braziliensis* and *Leishmania infantum*, respectively.

The y-axis of each of FIGS. 6 and 7 represents the percentage of parasite growth, and the x-axis represents the peptide concentration (µM). The symbol -o- represents the peptide MK61.

The example below illustrates the invention but does not limit it in any way.

EXAMPLE 1

Antibacterial, Antiviral and Antiparasitic Tests of the Peptides of Sequence "SEQ ID No. 1" AND "SEQ ID No. 2"

A. Synthesis of the Peptides

The peptides of sequence SEQ ID No. 1 (called "MK61" or "MK" hereinbelow) and of sequence SEQ ID No. 2 (called "GK36" or "GK" hereinbelow) were prepared by Proteogenix SA (France).

They are synthesised by the chemical route, purified by high performance liquid chromatography (HPLC) and checked by mass spectrometry. The degree of purity of each peptide is greater than 95%, and the molecular weights of the peptides GK36 and MK61 are 3676.57 g/mol and 6380.93 g/mol, respectively.

B. Antibacterial Tests

The bacteria *Escherichia coli* (Gram negative) and *Micrococcus luteus* (Gram positive) are cultivated in an LB (Luria-Bertani) culture medium with and without the peptides GK36 and MK61 to be tested. The bacterial growth is checked after incubation for one night at 37° C. by measuring the change in the absorbance value at 600 nanometres (A600) with the aid of a microplate spectrophotometer. The peptides MK61 and GK36 are incubated for 24 hours with the Gram negative and Gram positive bacteria. The minimum inhibitory concentration (MIC) of the synthetic peptides GK36 and MK61 represents the lowest peptide concentration that is sufficient to inhibit bacterial growth completely.

The results obtained are shown in FIG. 1 for the bacterium *Escherichia coli* (Gram negative) and in FIG. 2 for the bacterium *Micrococcus luteus* (Gram positive).

Conclusion

The peptides GK36 and MK61 have a marked activity against the Gram negative bacterium *E. coli* with MICs of 0.6 µM and 5 µM, respectively (see FIG. 1).

The peptides GK36 and MK61 also have a good activity against the Gram positive bacterium *Micrococcus luteus*, with MICs of 10 µm (see FIG. 2).

The peptides GK36 and MK61 therefore have a satisfactory antibacterial activity.

C. Antiviral Tests

1) Dengue Virus (Dengue Serotype 2)

(a) Inhibition of the Infection of Dendritic Cells by the Dengue Virus

The dendritic cells are the main target of the dengue virus ("Navarro-Sanchez et al., EMBO Rep. 2003 July, 4 (7): 723-8" and "Tassaneetrithep et al., J Exp Med., 2003, Apr. 7, 197(7): 823-9").

The dendritic cells are incubated for 3 hours at 37° C. in the presence of the dengue virus (they are infected at an "MOI" ("multiplicity of infection") of 0.4) with and without the peptides MK61 and GK36 to be tested, which are prepared at concentrations of 2.5 µg/ml and 12 µg/ml for MK61 and 2.5 µg/ml for GK36. The supernatant is then withdrawn and the cells are or are not brought into contact with peptide for 48 hours.

Real-time PCR analyses are then carried out. The cell viability is evaluated by flow cytometry, and no cell toxicity is observed.

The results obtained are shown in FIG. 3.

Conclusion

With the peptide MK61 at 12 µg/ml, the infection is lowered from 100% infection to 40% infection. Accordingly, the peptide MK61 at 12 µg/ml causes 60% inhibition of the infection of the dendritic cells. A dose-dependent inhibition is noted for the peptide MK61.

The peptide GK36 at 2.5 µg/ml causes 35% inhibition of the infection.

The peptides GK36 and MK61 therefore have a satisfactory antiviral activity.

(b) Inhibition of the Infection of C6/36 Cells by the Dengue Virus

The C6/36 cells of *Aedes albopictus* mosquitoes are incubated for one hour at 4° C. with the various dengue viruses ((serotype 1) "DENV-1" or (serotype 2) "DENV-2" or (serotype 3) "DENV-3" or (serotype 4) "DENV-4") (with "PFUs" ("plaque forming units") of 1). The cells are then washed three times and incubated for 12 hours or 24 hours at 28° C. in the presence or absence of the peptides GK36 and MK61 to be tested, which are each prepared at concentrations of 5 µg/ml or 10 µg/ml.

RT-PCR analyses are then carried out on the cell pellets in order to detect the presence of the dengue virus.

Figure 4:
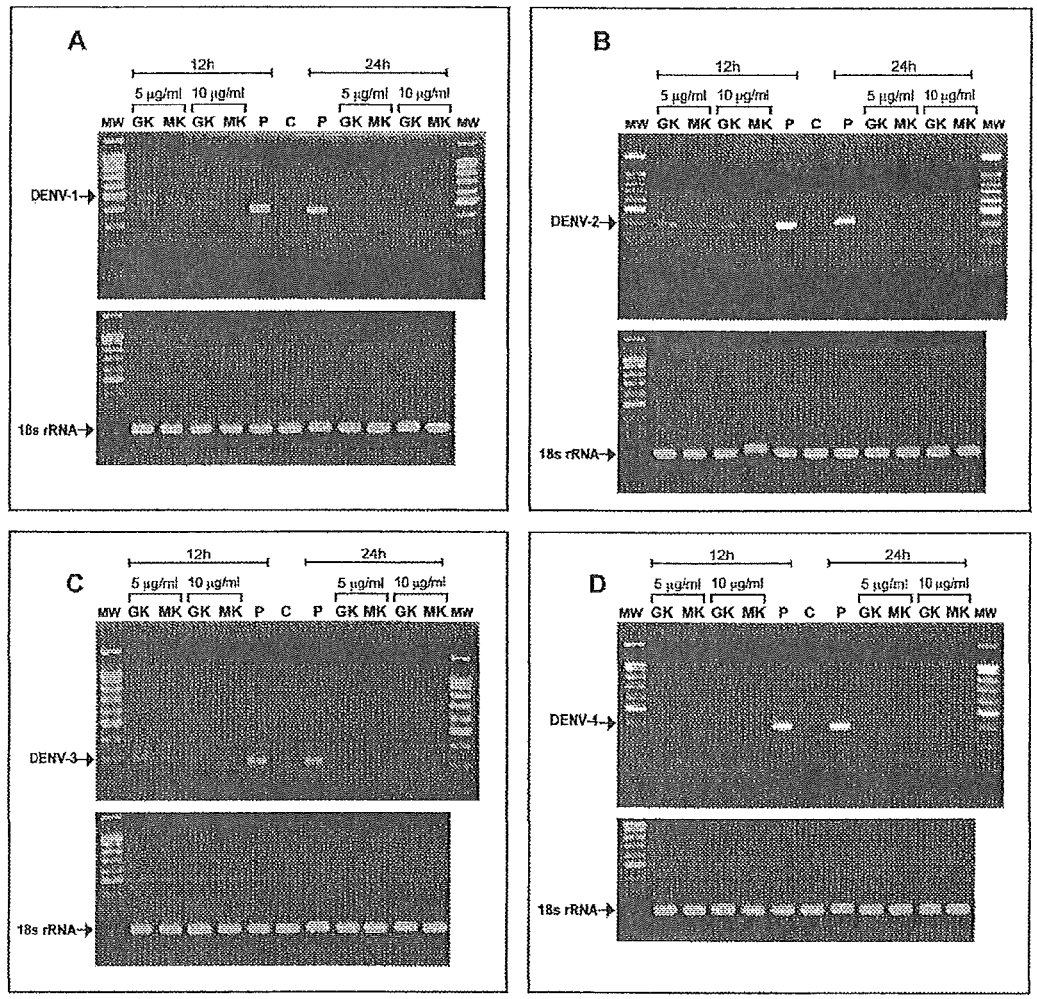

The results obtained are shown in FIG. 4 (A, B, C or D).

The letter P means that the control is positive, that is to say the cells are infected.

The letter C means that the control is negative, that is to say the cells recovered after 24 hours are not infected.

The letter M denotes the molecular weight marker.

The results show a considerable reduction in the production of virus in the presence of the peptides GK36 and MK61, in a dose-dependent manner (better inhibition of the infection is observed at 10 µg/ml than at 5 µg/ml ). A better inhibiting effect of the peptides is also noted with 24 hours' exposure as compared with the time of 12 hours. In view of the intensity of the bands, it is noted that the peptide MK is slightly more effective than the peptide GK.

The visibility by RT-PCR of the 18SrRNa gene (housekeeping gene) on the cell pellets shows that all the conditions exhibit the same amount of RNA.

Conclusion

The peptides GK36 and MK61 inhibit the infection of the C6/36 cells of *Aedes albopictus* mosquitoes by the dengue virus (dengue-1 virus, dengue-2 virus, dengue-3 virus and dengue-4 virus).

The effect is dose-dependent and is more pronounced after 24 hours. It is also noted that the peptide MK61 is more effective than the peptide GK36.

2) Chikungunya Virus

The cells, which come from the human cell line HEK-293T (human embryonic kidney 293), are incubated for 2 hours at 37° C. in the presence of CHIKV-147-2 GFP virus (they are infected at an "MOI" of 1) with and without the peptides GK36 and MK61 to be tested, which are each prepared at concentrations of 10 µg/ml, 50 µg/ml and 80 µg/ml. The supernatant is then withdrawn and the cells are or are not brought into contact with peptides for 48 hours. The percentage of cells infected corresponds to the percentage of GFP ("green fluorescent protein") cells visualised by flow cytometry (10,000 cells were counted per condition).

The results obtained are shown in FIG. 5.

Conclusion

The peptide MK61 inhibits the infection of the HEK-293T cells very effectively and in a dose-dependent manner, as was observed for the dengue virus.

The peptide GK36 also inhibits the infection of the HEK-293T cells, in a dose-dependent manner.

The results obtained both on the chikungunya virus and on the dengue virus therefore show that the peptides of sequence SEQ ID No. 1 and SEQ ID No. 2 are potent inhibitors of viral infection.

D. Antiparasitic Tests

Determination of Leishmaniasis Activity

Promastigotes of *Leishmania infantum* (strain MHOM/MA/67/ITMAP-263) and of *Leishmania braziliensis* (strain MHOM/BR/75M2904) expressing the luciferase gene were used to test the anti-leishmaniasis activities of the antimicrobial peptide MK61 in the manner described previously (Sereno et al., Antimicrob Agents Chemother. 2001 April; 45(4): 1168-73). Briefly, promastigote forms were inoculated in an amount of 10⁵ in 100 μl of medium, in 96-well plates, and then the peptide was added 4 hours later and the plates were incubated again for 72 hours.

The luciferase activity was then evaluated in order to determine the percentage growth of the parasites. The results are expressed as the "RLU" ("relative light unit") index.

RLU index=(RLU in the treated wells/RLU in the control wells)×100.

The results obtained are shown in FIGS. 6 and 7, which represent the incubation of the promastigotes expressing the luciferase gene for 72 hours at 37° C. with the peptide MK61.

Conclusion

The peptide MK61 has the ability to kill *leishmanias*. More particularly, the peptide has an antiparasitic activity on the two *leishmania* strains (*Leishmania infantum* and *Leishmania braziliensis*) with minimum inhibitory concentrations of from 20 to 40 μM.

The invention claimed is:

1. A medicament comprising an antimicrobial peptide, comprising the amino acid sequence of SEQ ID NO: 1 or the amino acid sequence of SEQ ID NO: 2, wherein the amino acid sequence of SEQ ID NO: 2 represents a fragment of the sequence SEQ ID NO: 1.

2. A medicament according to claim 1 for the treatment of at least one of a bacterial or a viral infection.

3. A medicament according to claim 2 for the treatment of a bacterial infection.

4. A medicament according to claim 3, wherein the bacterial infection is caused by Gram positive and/or Gram negative bacteria.

5. A medicament according to claim 1 for the treatment of a viral infection.

6. A medicament according to claim 5, wherein the viral infection is caused by a dengue virus and/or a chikungunya virus.

7. Antimicrobial peptide, comprising the amino acid sequence of SEQ ID NO: 1, for the treatment of bacterial, viral and parasitic infections.

8. Peptide according to claim 7 for the treatment of parasitic infections caused by the parasite *Leishmania braziliensis* and/or by the parasite *Leishmania infantum*.

9. Peptide according to claim 7 for the treatment of parasitic infections.

10. Pharmaceutical composition, comprising a therapeutically effective amount of the medicament, according to claim 1 in association with a pharmaceutically acceptable carrier.

11. Composition according to claim 10 for administration by the injectable route.

12. Composition according to claim 10 for administration in topical form.

13. The medicament according to claim 10, wherein the antimicrobial peptide comprises the amino acid sequence of SEQ ID NO: 1.

14. The medicament according to claim 1, wherein the antimicrobial peptide comprises the amino acid sequence of SEQ ID NO: 2.

15. A method for inhibiting the infection of a human cell by a dengue virus or a chikungunya virus comprising contacting the human cell with an effective amount of a composition comprising a peptide comprising the amino acid sequence of at least one of SEQ ID NO: 1 or SEQ ID NO: 2.

16. A method for treating an infection comprising administering to an infected animal an effective amount of a composition comprising a peptide comprising the amino acid sequence of at least one of SEQ ID NO: 1 or SEQ ID NO: 2.

17. The method of claim 16 wherein the infection is caused by a bacteria.

18. The method of claim 16 wherein the infection is caused by a virus.

19. The method of claim 18 wherein the virus is a dengue virus or a chikungunya virus

* * * * *

SEQUENCE LISTING

```
<160> NUMBER OF SEQ ID NOS: 3

<210> SEQ ID NO 1
<211> LENGTH: 61
<212> TYPE: PRT
<213> ORGANISM: Artificial sequences
<220> FEATURE:
<223> OTHER INFORMATION: antimicrobial peptides

<400> SEQUENCE: 1

Met Asn Met Asn Phe Thr Lys Leu Phe Ala Ile Val Leu Leu Ala Ala
1               5                   10                  15

Leu Val Leu Leu Gly Gln Thr Glu Ala Gly Gly Leu Lys Lys Leu Gly
            20                  25                  30

Lys Lys Leu Glu Gly Ala Gly Lys Arg Val Phe Lys Ala Ser Glu Lys
        35                  40                  45

Ala Leu Pro Val Val Gly Ile Lys Ala Ile Gly Lys
    50                  55                  60

<210> SEQ ID NO 2
<211> LENGTH: 36
<212> TYPE: PRT
<213> ORGANISM: Artificial sequences
<220> FEATURE:
<223> OTHER INFORMATION: antimicrobial peptides

<400> SEQUENCE: 2

Gly Gly Leu Lys Lys Leu Gly Lys Lys Leu Glu Gly Ala Gly Lys Arg
1               5                   10                  15

Val Phe Lys Ala Ser Glu Lys Ala Leu Pro Val Val Gly Ile Lys
            20                  25                  30

Ala Ile Gly Lys
        35

<210> SEQ ID NO 3
<211> LENGTH: 25
<212> TYPE: PRT
<213> ORGANISM: Artificial sequences
<220> FEATURE:
<223> OTHER INFORMATION: antimicrobial peptides

<400> SEQUENCE: 3

Met Asn Met Asn Phe Thr Lys Leu Phe Ala Ile Val Leu Leu Ala Ala
1               5                   10                  15

Leu Val Leu Leu Gly Gln Thr Glu Ala
            20                  25
```